US008500773B2

(12) United States Patent
Nardone et al.

(10) Patent No.: US 8,500,773 B2
(45) Date of Patent: Aug. 6, 2013

(54) SPRING DETACH JOINT FOR DELIVERING A DETACHABLE IMPLANTABLE DEVICE (75) Inventors: Christopher Nardone, N. Chelmsford, MA (US); Nicholas Fedas, Amherst, NH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1325 days.

(21) Appl. No.: 12/183,659

(22) Filed: Jul. 31, 2008

(65) Prior Publication Data
US 2009/0036877 A1    Feb. 5, 2009

Related U.S. Application Data (60) Provisional application No. 60/953,329, filed on Aug. 1, 2007.

(51) Int. Cl.
*A61M 29/00*          (2006.01)
(52) U.S. Cl.
USPC ........................... 606/200; 606/108; 606/191
(58) Field of Classification Search
USPC .................................................. 606/108, 191
See application file for complete search history.

(56) References Cited

U.S. PATENT DOCUMENTS

| | | | | |
|---|---|---|---|---|
| 430,849 A | * | 6/1890 | Groth | 606/206 |
| 3,837,690 A | * | 9/1974 | Fraser et al. | 285/319 |
| 4,792,320 A | * | 12/1988 | Nickel | 464/181 |
| 4,827,941 A | * | 5/1989 | Taylor et al. | 600/434 |
| 4,846,193 A | * | 7/1989 | Tremulis et al. | 600/585 |
| 4,990,151 A | * | 2/1991 | Wallsten | 606/108 |
| 5,029,908 A | * | 7/1991 | Belisaire | 285/323 |
| 5,078,702 A | * | 1/1992 | Pomeranz | 604/524 |
| 5,217,484 A | * | 6/1993 | Marks | 606/200 |
| 5,304,195 A | | 4/1994 | Twyford, Jr. et al. | |
| 5,370,134 A | * | 12/1994 | Chin et al. | 128/898 |
| 5,480,423 A | * | 1/1996 | Ravenscroft et al. | 623/1.11 |
| 5,511,559 A | * | 4/1996 | Vance | 600/585 |
| 5,601,600 A | * | 2/1997 | Ton | 606/206 |
| 5,609,608 A | * | 3/1997 | Benett et al. | 606/205 |
| 5,702,418 A | * | 12/1997 | Ravenscroft | 623/1.11 |
| 5,820,612 A | * | 10/1998 | Berg | 604/527 |
| 5,891,130 A | * | 4/1999 | Palermo et al. | 606/1 |
| 5,895,385 A | | 4/1999 | Guglielmi et al. | |
| 5,925,059 A | | 7/1999 | Palermo et al. | |

(Continued)

FOREIGN PATENT DOCUMENTS

| | | |
|---|---|---|
| EP | 0 829 236 A1 | 3/1998 |
| WO | WO 93/11719 A1 | 6/1993 |
| WO | WO 93/11825 A1 | 6/1993 |

OTHER PUBLICATIONS

Boston Scientific Corp. "Interlock™ Fibered IDC Occlusion System—Pioneering Precision" 2006 (2 pages).

(Continued)

*Primary Examiner* — Nicholas Lucchesi
*Assistant Examiner* — Scott Medway
(74) *Attorney, Agent, or Firm* — Bingham McCutchen LLP (57) ABSTRACT Methods and systems for delivering an implantable device to a target site, using a detachable link. The system can include an embolic coil mated to a delivery wire via a detachable link comprising first and second engaging members. When the detachable link is delivered through a catheter, the first and second engaging members are configured to self-detach.

9 Claims, 9 Drawing Sheets

U.S. PATENT DOCUMENTS

| | | | |
|---|---|---|---|
| 6,214,036 B1 * | 4/2001 | Letendre et al. | 623/1.11 |
| 6,238,415 B1 * | 5/2001 | Sepetka et al. | 606/213 |
| 6,254,612 B1 * | 7/2001 | Hieshima | 606/108 |
| 6,319,287 B1 * | 11/2001 | Frimberger | 623/23.64 |
| 6,800,085 B2 * | 10/2004 | Selmon et al. | 606/198 |
| 6,843,802 B1 * | 1/2005 | Villalobos et al. | 623/1.12 |
| 6,858,034 B1 * | 2/2005 | Hijlkema et al. | 606/108 |
| 6,911,016 B2 * | 6/2005 | Balzum et al. | 604/95.04 |
| 6,936,058 B2 * | 8/2005 | Forde et al. | 606/200 |
| 7,022,018 B2 * | 4/2006 | Koga | 464/52 |
| 7,338,518 B2 * | 3/2008 | Chobotov | 623/1.12 |
| 7,347,866 B2 * | 3/2008 | Daignault et al. | 606/191 |
| 7,641,687 B2 * | 1/2010 | Chinn et al. | 623/2.4 |
| 7,678,129 B1 * | 3/2010 | Gesswein et al. | 606/200 |
| 7,879,065 B2 * | 2/2011 | Gesswein et al. | 606/200 |
| 2005/0004598 A1 | 1/2005 | White, Jr. et al. | |
| 2007/0055380 A1 * | 3/2007 | Berelsman et al. | 623/19.11 |
| 2007/0141099 A1 | 6/2007 | Buiser et al. | |
| 2007/0142859 A1 | 6/2007 | Buiser et al. | |
| 2007/0142893 A1 | 6/2007 | Buiser et al. | |

OTHER PUBLICATIONS

Murphy, K.J. et al. "Mechanical Detachable Platinum Coil: Report of the European Phase II Clinical Trial in 60 Patients" *Radiology* 219:541-544 (2001).

Murphy, K.J. et al. "A Report of the Clinical Use of the Detach-18 Mechanical Detachable Platinum Coil in 41 Patients" *Am. J. Neuroradiol. (AJNR)* 22:341-344 (Feb. 2001).

* cited by examiner

SPRING DETACH JOINT FOR DELIVERING A DETACHABLE IMPLANTABLE DEVICE

This application claims priority to U.S. Provisional Application No. 60/953,329, entitled "SPRING DETACH JOINT FOR DELIVERING A DETACHABLE IMPLANTABLE DEVICE," filed Aug. 1, 2007.

TECHNICAL FIELD

The present invention relates to the field of detachable implantable devices and more specifically to the methods and systems for delivery of these devices.

BACKGROUND

The endovascular treatment of a variety of maladies throughout the body is an increasingly more important form of therapy. One such procedure uses embolizing coils to occlude a target site by posing a physical barrier to blood flow and/or by promoting thrombus formation at the site. Such treatments can be useful where it is desired to reduce vascularization, including treatments for aneurysms and cancer.

Coils have typically been placed at a desired site within the vasculature using a catheter and a pusher. As a first step, a flexible, small diameter catheter can be guided to the target site through the use of delivery wires or by flow-directed means such as balloons placed at the distal end of the catheter. Once the site has been reached, the catheter lumen is cleared by removing the delivery wire (if a delivery wire has been used), and the coil is placed into the proximal open end of the catheter and advanced through the catheter with a pusher. Pushers are wires having a distal end that is adapted to engage and push the coil through the catheter lumen as the pusher is advanced through the catheter. When the coil reaches the distal end of the catheter, it is discharged from the catheter by the delivery wire into the vascular site.

Several techniques have been developed to enable more accurate placement of coils within a vessel. In one technique the coil is bonded via a metal-to-metal joint to the distal end of the pusher. The pusher and coil are made of dissimilar metals. The coil-carrying pusher is advanced through the catheter to an anatomic site and a small electrical current is passed through the pusher-coil assembly. The current causes the joint between the pusher and the coil to be severed via electrolysis. The pusher may then be retracted leaving the detached coil at a target position within the vessel. In addition to enabling accurate coil placement, the electric current may facilitate thrombus formation at the coil site. A perceived disadvantage of this method is that the electrolytic release of the coil requires a period of time so that rapid detachment of the coil from the pusher does not occur.

Another technique for detaching an embolic coil uses a mechanical connection between the coil and the pusher. For example, one such device uses interlocking clasps which are secured to each other by a control wire that extends the length of the catheter. Retraction of the control wire uncouples the coil from the pusher. While mechanical connections between coils and pusher wires provide for quick detachment, such detachable coils require additional control mechanisms (i.e., control wires) to deploy the coil.

Accordingly, while conventional systems provide effective coil delivery, further improvements that facilitate delivery, while reducing the chance of premature deployment or jamming, would be beneficial.

SUMMARY OF THE INVENTION

Disclosed herein are methods and systems for delivering an implantable device to a target site using a detachable link. The described systems overcome the drawbacks of conventional mechanical interlocks and provide a more robust coil delivery system. In addition, the systems can reduce the chance of premature device detachment and/or jamming. In one such embodiment, the systems can include a detachable link designed to inhibit premature detachment of the detachable link during delivery of the implantable device through a catheter lumen.

For example, the implant delivery system can include an elongate catheter and an implantable device mated to a delivery wire via a detachable link comprising first and second engaging members. The first engaging member can include an expandable member adapted to move between a first and a second position. In the first position, an outer diameter of the first engaging member is larger than an inner diameter of the catheter, while in the second position the outer diameter is smaller than the inner diameter of the catheter. When the detachable link is inserted into the catheter, the first engaging member moves from the first position to the second position.

The second engaging member can include an outer surface adapted for receipt at least partially within the first engaging member when the first engaging member is in the first position. Moving the first engaging member from the first to the second position locks the second engaging member within the first engaging member. For example, the second engaging member can be configured to mate with an inner surface of the first engaging member when the first engaging member is in the second position.

In one aspect, the expandable member includes an inner cavity defined by an outer wall. At least a portion of the wall can define the expandable member. For example, the wall can be formed of a flexible, elastic, and/or compressible material. At least a portion of the wall can have a diameter larger than an inner diameter of the catheter. When the detachable link is inserted into the catheter, the inner wall of the catheter can move the first engaging member from the first position to the second position by flexing, compressing, and/or bending the wall. In the second position, a diameter of the cavity is reduced sufficiently to cause the inner surface of the cavity to mate with the outer surface of the second engaging member. Conversely, once the detachable link exits the distal end of the catheter, the wall can expand and allow the second engaging member to detach from the first engaging member.

In another aspect, the wall is biased in the first position. For example, as described further below, the wall can be formed of a resilient material. After the detachable link leaves the catheter and the catheter no longer compresses the first engaging member, the wall can move toward its pre-insertion configuration.

In one aspect, the inner surface of the first engaging member can frictionally engage with the second engaging member when the first engaging member is in the second position. Alternatively, or additionally, the first and second engaging members can mechanically mate with one another. For example, the outer surface of the second engaging member can include a recess adapted to receive a portion of the expandable member when the expandable member is in the second position.

In another embodiment, a detachable link system is provided. The system includes an elongate device having a lumen and a detachable link comprising first and second engaging members. The first engaging member has a wall including an inner and outer surface and a locking member adapted to move, relative to the wall, between a first and a second position. In the first position, an outer diameter of the first engaging member is larger than an inner diameter of the lumen and in the second position the outer diameter of the first engaging member is smaller than the inner diameter of the lumen. Also, in the first position an inner diameter of the first engaging member is larger than the inner diameter of the first engaging member in the second position.

The second engaging member has an outer surface shaped and sized for receipt at least partially within the inner surface of the first engaging member when the locking member is in the first position. When the locking member is in the second position, the locking member can be adapted to mate with the second engaging member and inhibit detaching of the detachable link.

In one aspect, the detachable link has an elongate body that extends in a longitudinal direction and the locking member includes an elongate body that extends in a non-longitudinal direction with respect to the detachable link.

In another embodiment described herein, the first engaging member includes first and second arms that define a mating area therebetween. At least one of the first and second arms is adapted to articulate between a locked and unlocked position. In the unlocked position, an outer distance between outer surfaces of the arms is larger than an inner diameter of the lumen and wherein in the locked position the outer distance is smaller than the inner diameter of the lumen.

The second engaging member can have outer surface shaped and sized for receipt at least partially between inner surfaces of the arms in the unlocked position and shaped and sized to inhibit movement out of the mating area when the arms are in the locked position.

In a still further aspect, at least one of the first and second arms is biased in the unlocked position. For example, at least one of the first and second arms can be mated to the first engaging member via a living hinge.

BRIEF DESCRIPTION OF THE DRAWINGS

The accompanying drawings, which are incorporated in and constitute a part of this specification, provide exemplary embodiments of the invention and, together with the description, serve to explain the principles of the invention.

DETAILED DESCRIPTION OF THE DRAWINGS

Disclosed herein are methods and systems for delivering an implantable device to a target site, and more particularly, an implantable device detachable from a pusher wire. The detachable, implantable device can be mated to a delivery wire via a detachable link that comprises first and second engaging members. In one aspect the detachable link includes features that inhibit unwanted detachment during delivery through a catheter. In particular, the detachable link can inhibit detachment when positioned in a catheter and can allow delivery of the implantable device when the implantable device reaches a target area. In addition, the detachable link can minimize jamming during delivery through a catheter.

Figures 1A, 1B:
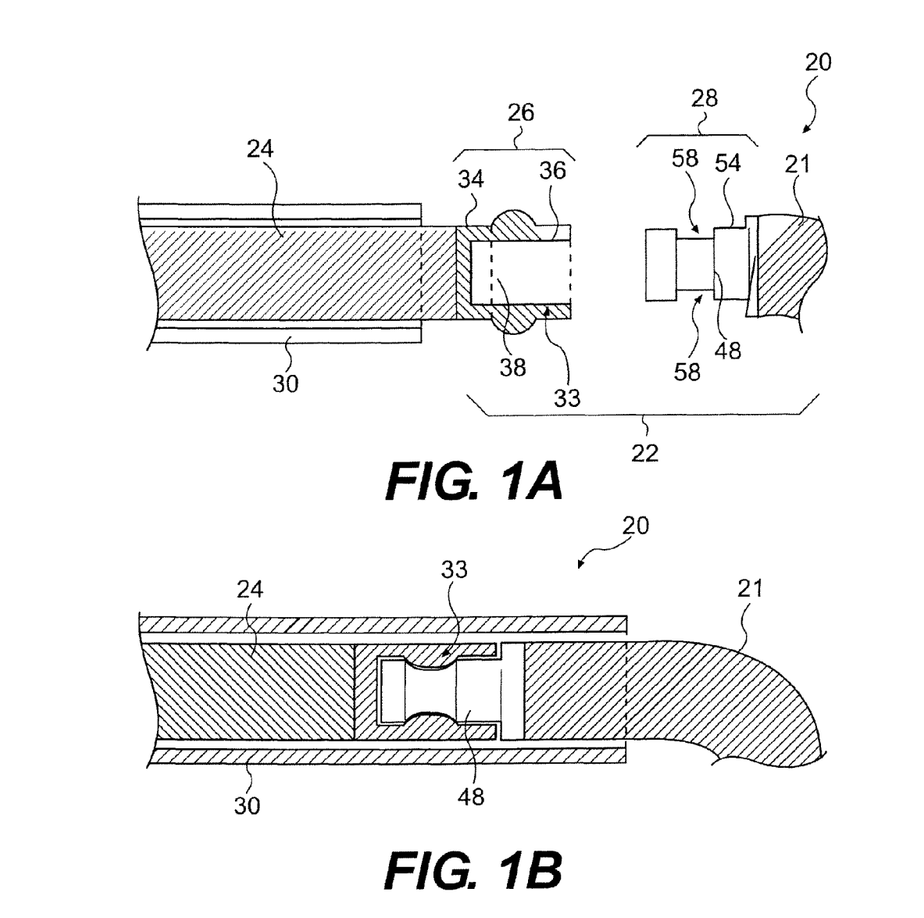
FIG. 1A illustrates a cross-sectional view of an embodiment of the implant delivery system in an unmated configuration.
FIG. 1B illustrates a cross-sectional view of FIG. 1A in a mated configuration inside the catheter.

FIG. 1A illustrates a system 20 for delivering an implantable device, in this case an embolic coil 21, to a target site. The system includes a detachable link 22 for releasably joining the embolic coil 21 and a delivery wire 24. In one aspect, the detachable link 22 can include a first engaging member 26 and a second engaging member 28 that are sized and shaped to mate with one another. As discussed below, engaging members 26, 28 can have a variety of shapes and/or sizes that provide a detachable connection that self-detaches after exiting the distal end of a catheter 30.

One skilled in the art will appreciate that the embolic coil 21 and delivery wire 24 are merely representative of the environment in which the detachable link 22 operates, and that a variety of alternative medical devices could be substituted. For example, the systems described herein could be used to deliver a variety of implantable devices in addition, or as an alternative, to the embolic coil 21. Similarly, the delivery wire 24 represents the variety of control devices for moving an implantable device through a lumen of a medical instrument. Further, while coil delivery system 20 is generally described with respect to the detachable link 22 traveling through catheter 30, one skilled in the art will appreciate that detachable link 22 may travel through a variety of medical instruments, such as, for example, introducers, and that the methods and devices described herein are equally applicable to any medical device having a lumen for the delivery of a detachable, implantable device. In particular, the term "catheter" as used herein can refer to the variety of medical devices having an inner lumen adapted for receiving a medical instrument and/or implantable device.

Figure 2A:
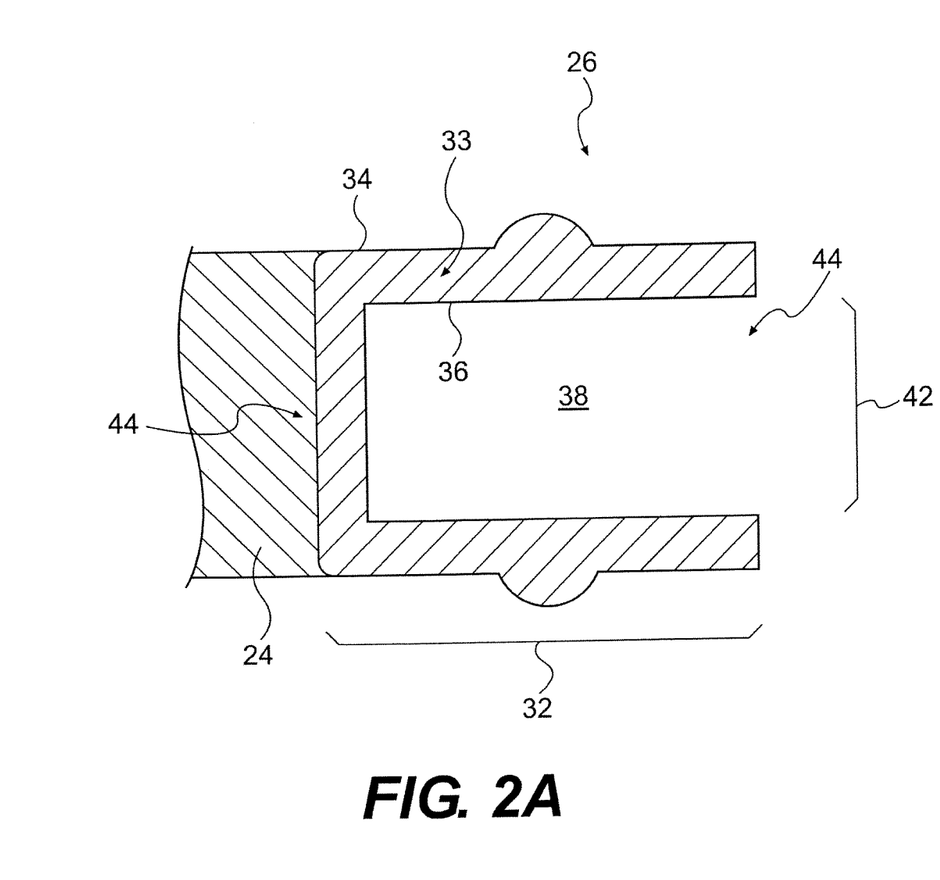
FIG. 2A illustrates a cross-sectional view of the first engaging member.

FIGS. 1A and 1B illustrate exemplary implant delivery system 20 in a detached and attached configuration, respectively. As shown, the first and second engaging members 26, 28 have a male/female configuration, where the first engaging member 26 is adapted to receive at least a portion of the second engaging member 28. In particular, as shown in FIG. 2A, first engaging member 26 has a generally elongate body 32 having an outer surface 34, an inner surface 36 and a wall 33 therebetween. Wall 33 defines an open interior portion of body 32, shown as cavity 38. A distal portion 40 of body 32 can include an opening 42 for ingress to cavity 38, while a proximal portion 44 of body 32 mates with delivery wire 24. In one aspect, first engaging member 26 is integrally formed with delivery wire 24. Alternatively, the first engaging member 26 can be fixedly mated to the delivery wire 24 in a variety of ways, including, for example, via a mechanical connection and/or weld.

Figure 2B:
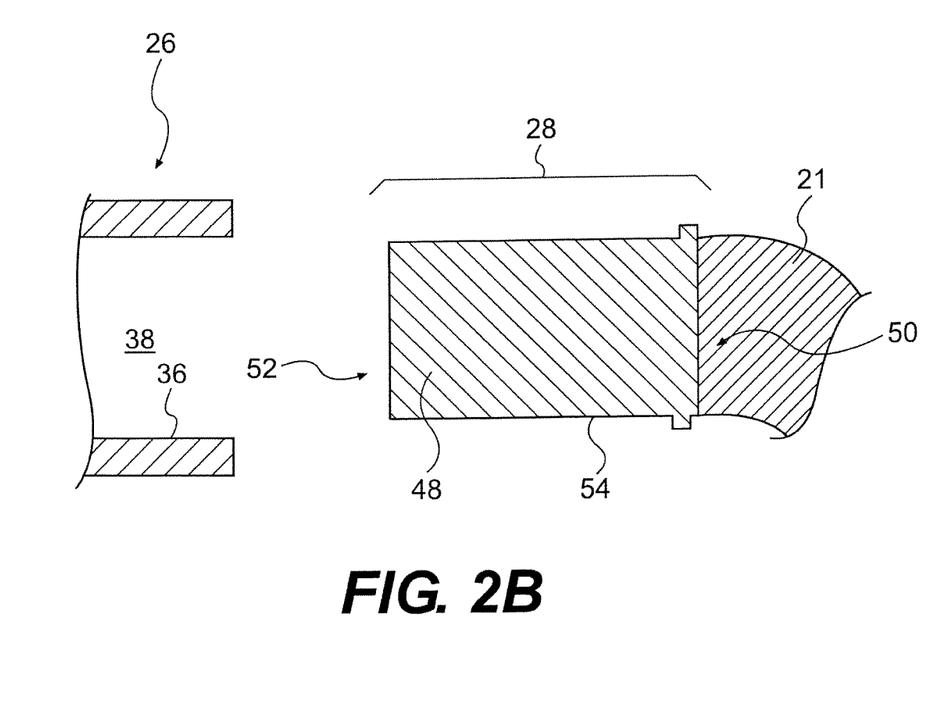
FIG. 2B illustrates a cross-sectional view of the second engaging member.

FIG. 2B illustrates an exemplary embodiment of second engaging member 28 including a body 48 extending between a distal portion 50 for mating with coil 21 and a proximal end 52. Body 48 can have an outer surface 54 configured for receipt at least partially within cavity 38 of first engaging member 26. In one aspect, the outer surface 54 of second engaging member 28 has a size and shape corresponding to the inner surface 36 of first engaging member 26. However, second engaging member 28 can have a variety of alternative shapes and sizes that allow the second engaging member 28 to mechanically and/or frictionally mate with the first engaging member 26. The distal portion 50 of second engaging member 28 can mate to coil 21 via a permanent or semi-permanent connection. For example, the second engaging member 28 can be machined from a portion of the coil. Alternatively, the second engaging member 28 can be fixedly mated, for example, by way of a mechanical connection and/or welding.

Although FIGS. 2A and 2B show the first and second engaging members 26, 28 mated with the delivery wire and coil, respectively, other configurations are possible. For example, system 20 can have a male engaging member extending from the delivery wire and a female engaging member extending from the coil As shown in FIGS. 1A and 1B, the dimensions of first engaging member, 26 change when inserted into catheter 30. First engaging member 26 has a first outer diameter when outside catheter 30 and a second, smaller outer diameter when constrained by catheter 30. In particular, at least a portion of wall 33 of first engaging member 26 can radially expand and/or contract to move between a unlocked position (FIG. 1A) and a locked position (FIG. 1B). In the unlocked position, the outer surface 34 of first engaging member 26 can have a first diameter that is larger than an inner diameter of catheter 30. Conversely, once inserted into catheter 30, outer surface 34 has a diameter smaller than then inner diameter of the catheter.

As the outer diameter of the first engaging member changes, the inner diameter of cavity 38 also varies. In the unlocked position, the diameter of cavity 38 is larger than an outer diameter of the second engaging member 28, which allows the second engaging member 28 to move into and out of cavity 38 of first engaging member 26. As the first engaging member 26 is moved into catheter 30, the diameter of inner surface 36 is reduced such that inner surface 36 of first engaging member 26 can mechanically and/or frictionally mate with the outer surface 54 of second engaging member 28. Thus, when the detachable link is constrained by the catheter, the detachable link moves into the "locked" position.

While the relative size of the inner and outer surfaces of the first and second engaging member are described in terms of diameter, it should be appreciated that the term "diameter" is used for convenience and that cavity 38 and second engaging member body 48 can have a variety of shapes, including non-circular shapes. The term "diameter" can apply to any cross-sectional distance that varies when the detachable link is moved into and out of a catheter.

Figure 3A:
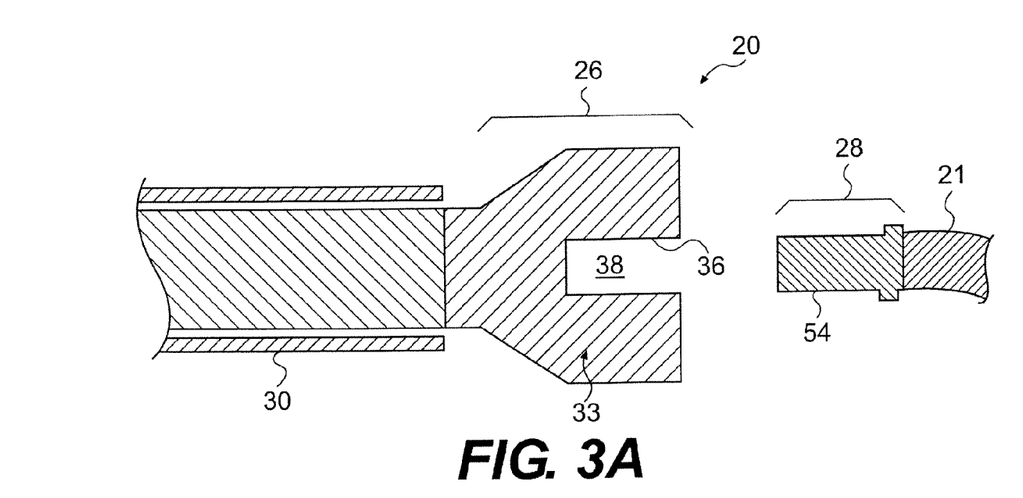
FIG. 3A illustrates a cross-sectional view of another embodiment of the implant delivery system in an unmated configuration.
Figure 3B:
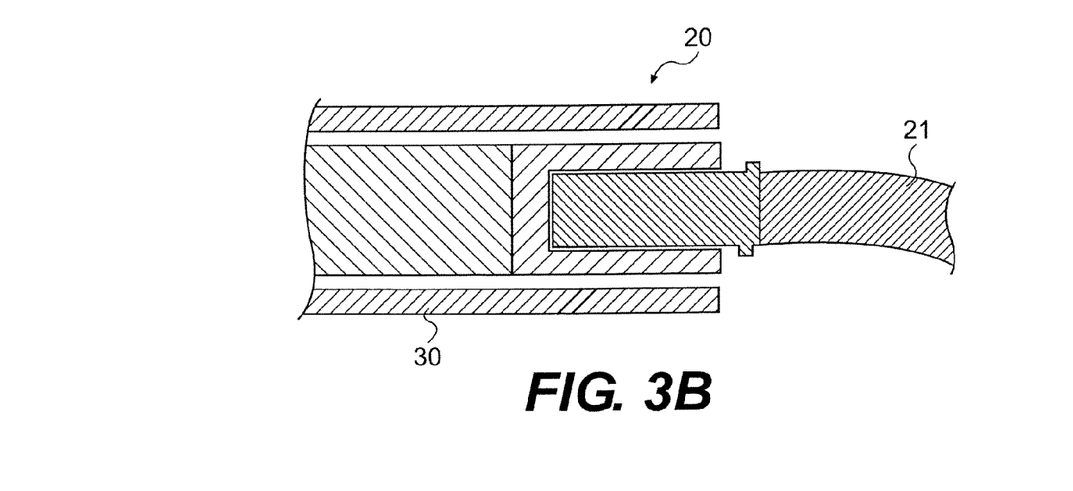
FIG. 3B illustrates a cross-sectional view of FIG. 3A in a mated configuration inside the catheter.

In one embodiment, as shown in FIGS. 3A and 3B, wall 33 can be formed, at least in part, of a compressible material that allows the first engaging member to move from an unlocked to a locked position when inserted into the catheter 30. As mentioned above, the diameter of the outer surface of the first engaging member 26 is larger than an inner diameter of the catheter 30. When the first engaging member 26 is inserted into catheter 30, the diameter of the inner and outer surfaces of the first engaging member are reduced. The force applied by the catheter walls causes the inner surface 36 of the first engaging member 26 to frictionally engage the outer surface 54 of the second engaging member 28. Conversely, once the detachable link exits the distal end of the catheter, the compressible walls 33 can radially expand to allow delivery of the implantable device. In particular, the walls can be compressible and resilient.

In another aspect, wall 33 is formed of resilient and flexible and/or elastic material such that applying pressure to the outer surface of wall 33 cause cavity 38 to change its size and/or shape. In particular, the inner dimensions of catheter 30 can cause wall 33 to deform and/or deflect when the first engaging member is inserted into the inner lumen of catheter 30. When the first engaging member 26 is removed from the catheter, wall 33 radially expands, and moves towards its original configuration.

Figure 4A:
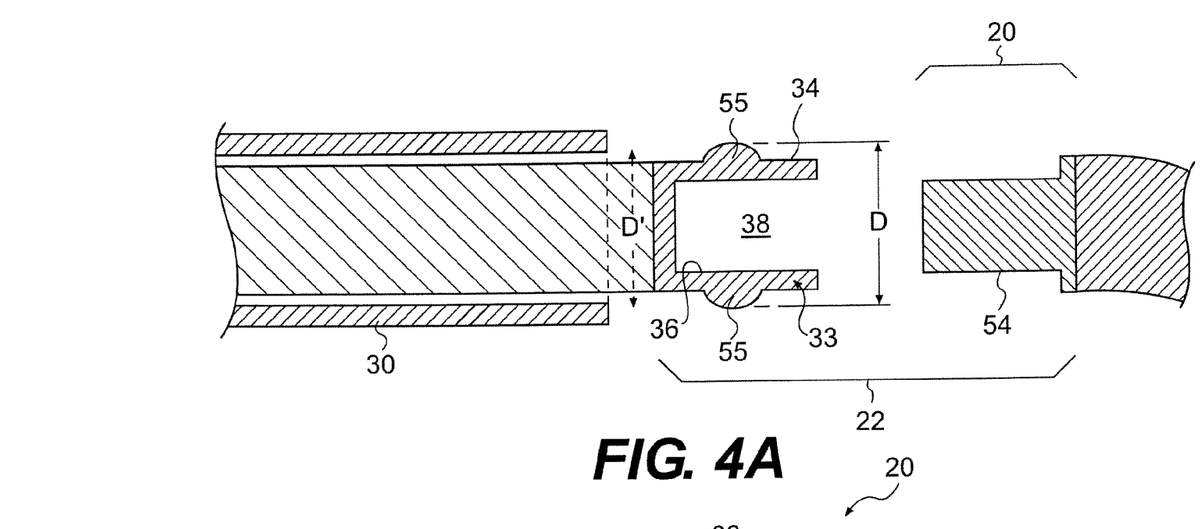
FIG. 4A illustrates a cross-sectional view of yet another embodiment of the implant delivery system in an unmated configuration.
Figure 4B:
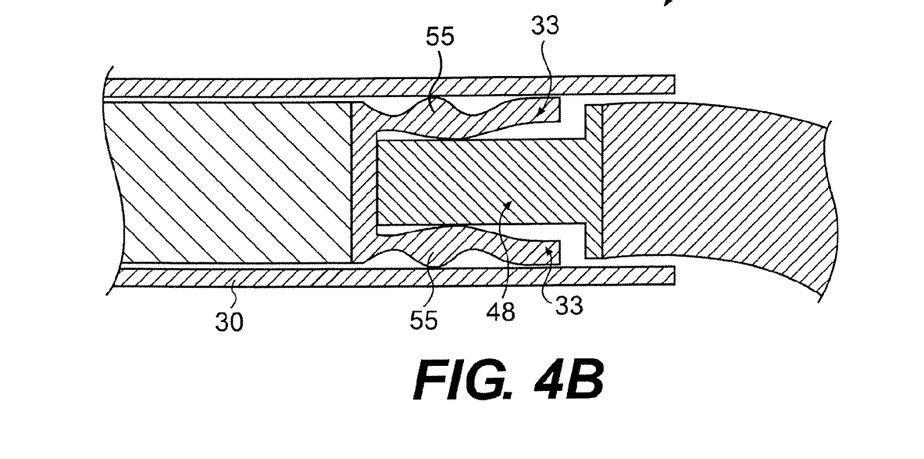
FIG. 4B illustrates a cross-sectional view of FIG. 4A in a mated configuration inside the catheter.

In another aspect, only a portion of wall 33 moves between a locked and unlocked position. For example, as shown in FIGS. 4A and 4B, wall 33 can include a rib or protrusion 55 that extends from outer surface 34 of the first engaging member 26. When unconstrained by catheter 30, the protrusion has an outer diameter D that is greater than the outer diameter of the outer surface 34 adjacent to the protrusion. When the first engaging member is inserted into catheter 30, the protrusion contacts the inner surface of the catheter lumen. Since the catheter lumen has a diameter D', which is smaller than the diameter D of the protrusion, wall 33 flexes inward and the inner surface 36 of wall 33 contacts the outer surface of the second engaging member 28. As shown in FIG. 4A, the outer diameter of the protrusion 55, when placed within catheter 30, reduces to a diameter smaller than the diameter D' of the catheter lumen. In particular, a portion of wall 33 adjacent to protrusion 55 bends inward toward cavity 38 to reduce the outer diameter of protrusion 55. In addition, the diameter of cavity 38 is reduced adjacent to protrusion 55, allowing inner surface 36 to mate with the outer surface 54 of the second engaging member 28.

The protrusion 55 can have unitary configuration such that the wall and protrusion are formed as a single body, or alternatively, the protrusion can be formed separately and mated with the outer surface of wall 33. In addition, protrusion 55 can be formed of the same or a different material as wall 33. In the illustrated embodiment, protrusion 55 extends around the entire circumference of wall 33. However, in another aspect, protrusion 55 can have a different shape and extend around only a portion of the outer surface of wall 33 and/or extend longitudinally with respect to the detachable link 22.

As mentioned above, the first and second engaging members can mate via a mechanical and/or frictional engagement when locked to one another. For example, when wall 33 is moved inward by catheter 33, the forced applied by the catheter is transmitted through the walls of the first engaging member 26 to the second engaging member 28. The forced applied by the inner surface 36 of the first engaging member 26 on the outer surface 54 of the second engaging member 28 can frictionally engage the first and second engaging members. In one aspect, the outer surface 54 of the second engaging member 28 can include surface features to facilitate frictional engagement.

In another aspect, second engaging member 28 can include a surface adapted to mechanically mate with the first engaging member 26. For example, in the locked configuration the inner surface 36 of the walls 33 can extend into a recess on the outer surface 54 of the second engaging member. For example, a portion of the flexible, compressible, and/or elastic wall can be forced into a recess in the outer surface of the second engaging member. In addition, the inner surface 36 of the first engaging member can include a protrusion for receipt in a recess in the outer surface of the second engaging member. As shown in FIGS. 1A and 1B, the outer surface of the second engaging member 28 includes a recess 58 to receive inner surface 36 of the first engaging member 26. In yet another aspect, the inner surface of wall 33 can include a recess and the outer surface of the second engaging member can include a corresponding protrusion.

Regardless of the material properties of wall 33 (e.g., flexible, compressible, and/or elastic), wall 33 can be resilient. When the first engaging member 26 is removed from catheter 30, resilient wall 33 can radially expand toward its pre-insertion configuration. Once wall 33 expands, the second engaging member 28 is no longer locked within the first engaging member 26 and the detachable link 22 can self-detach. However, some force may still be required to detach depending on, for example, the surface properties of the contact surfaces of the first and second engaging members (e.g., coefficient of friction) and the relative size of the first and second engaging members. For example, the contact surfaces can be formed of, and/or coated with, a low friction material to facilitate decoupling of the engaging members. Similarly, in the unlocked position, the first and second engaging members can mate with a clearance fit. The amount of space between the contact surfaces of the first and second engaging members, when the detachable link is in an unlocked position, can be chosen to minimize the force required for the first and second engaging members to self-detach.

Figure 5A:
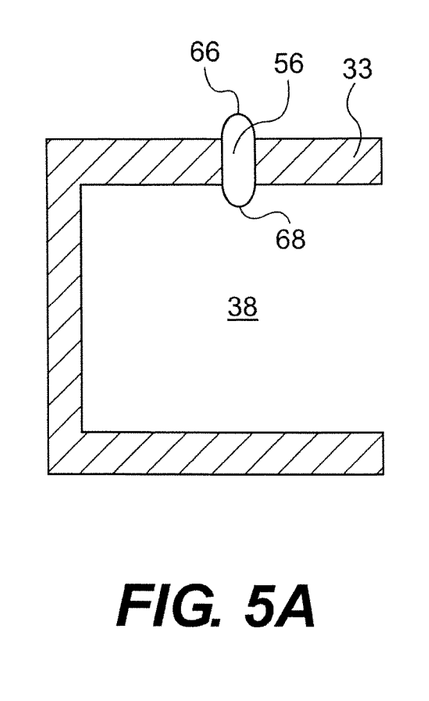
FIG. 5A illustrates a cross-sectional view of an embodiment of a locking member positioned in the wall of the first engaging member.
Figure 5B:
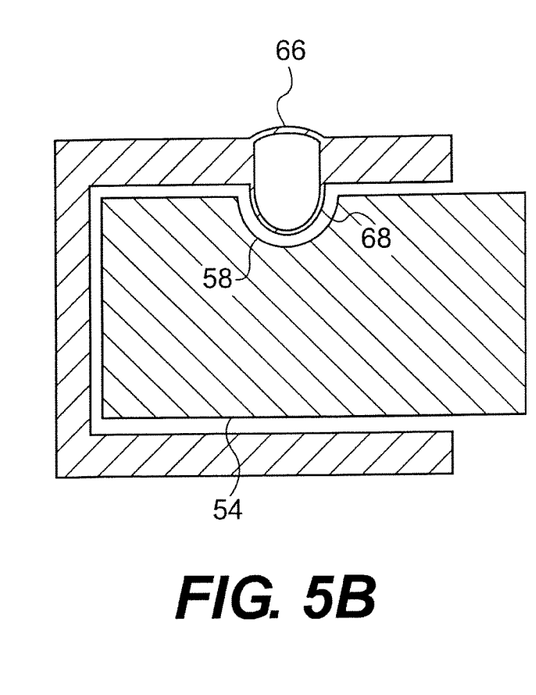
FIG. 5B illustrates a cross-sectional view of FIG. 5A with the locking member moved in a radial direction toward the inner cavity (in its compressed state when inside the catheter)

In another embodiment of system 20 described herein, instead of the inner surface of wall 33 moving between a locked and unlocked position, the first engaging member can include an articulating locking member that travels between a locked and unlocked position. In one aspect, the locking member can extend through wall 33 and move relative to the wall. The locking member can include an elongate body extending in a non-longitudinal direction with respect to the detachable link 22. For example, as illustrated in FIGS. 5A and 5B, locking member 56 is positioned in wall 33 and includes an elongate body having an upper catheter contacting surface 66 and a lower second engaging member contacting surface 68. The upper surface 66 of locking member 56 can be positioned to contact the inner surface of catheter 30 when inserted into the catheter, such that the inner surface of the catheter moves the locking member in a radial direction toward cavity 38. The lower surface 68 of locking member 56, when the detachable link is positioned in catheter 30, can mate with the outer surface of the second engaging member (FIG. 5B).

The upper and lower surfaces 66, 68 of locking member 56 can have a variety of shapes. In one aspect, the upper surface is configured to facilitate insertion of the detachable link into a catheter and to facilitate movement of the locking member between a locked and unlocked position. For example, the upper surface 66 can have a ramped configuration such as, for example, a semi-spherical or triangular shape.

The lower surface 68 can have a shape and size adapted to mate with the outer surface of the second engaging member. In one aspect, locking member 56 mechanically mates with the outer surface of the second engaging member 28. For example, lower surface 68 can have a shape generally corresponding to a portion of recess 58 in the outer surface of the second engaging member. Recess 58 can also have a shape and size larger than lower surface 68 so that lower surface 68 does not need to be exactly aligned with recess 58 to achieve a locked configuration. Recess 58, for example, can extend around the circumference of the outer surface of the second engaging member and/or can have a longitudinal width greater than the width of lower surface 68.

In addition, or alternatively, the locking member can frictionally mate with the second engaging member. For example, when the locking member is in the locked configuration, the lower surface 68 can frictionally engage the outer surface 54 of the second engaging member. In another aspect, the second engaging member body can be formed of a non-rigid material. For example, the second engaging member can be formed of a resilient material such that the locking member depresses a portion of the outer surface of the second engaging member in the locked position. In addition to facilitating locking of the first and second engaging members, the resilient second engaging member can bias the locking member in the unlocked position.

Figure 6:
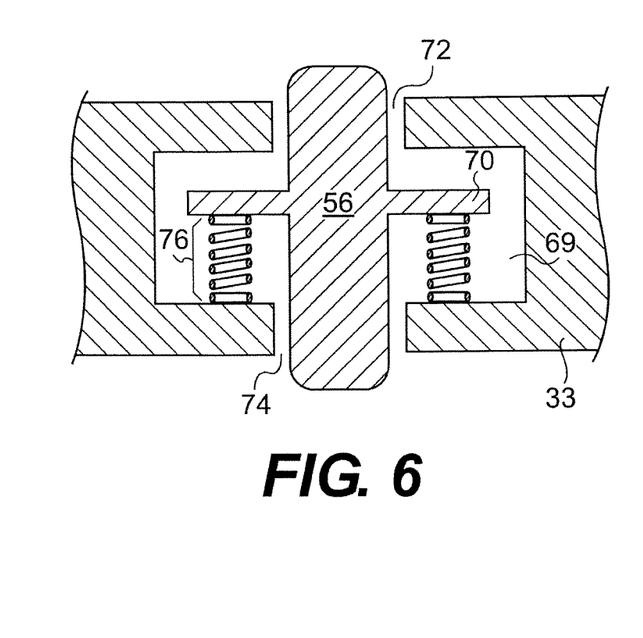
FIG. 6 illustrates a cross-sectional view of another embodiment of a locking member.

In one aspect, locking member 56 extends through an opening in wall 33. A portion of the locking member body can mate with wall 33 to allow the locking member to articulate, while limiting the travel of the locking member. FIG. 6 illustrates one exemplary configuration of locking member 56 positioned within an passageway 69 in wall 33. The locking member includes an area of greater width along its length defined by wing 70, which has a greater width than upper and lower apertures 72, 74 of passageway 69. Wing 70 allows locking member 56 to move relative to wall 33, but prevents the locking member from fully detaching from the first engaging member. In addition, locking member 56 can be biased in the unlocked position to allow the detachable link to self-detach when the locking member exits the catheter. In one aspect, a spring or resilient member 76 can contact wing 70 and bias the locking member in the unlocked position.

Figure 7:
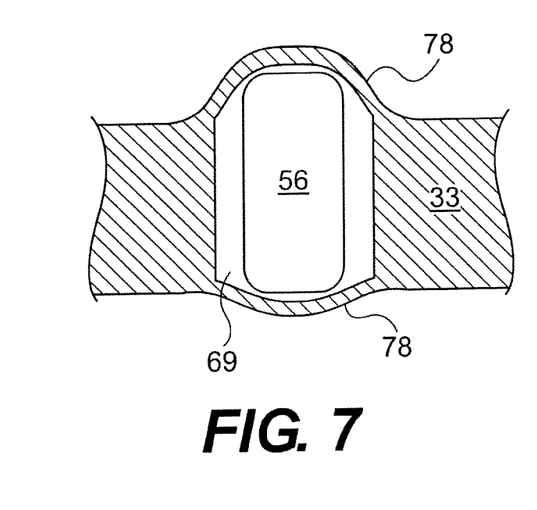
FIG. 7 illustrates a cross-sectional view of yet another embodiment of a locking member.

In another embodiment, the locking member is positioned within wall 33 such that the wall allows the locking member to articulate, but prevents the locking member from leaving the opening in the wall. FIG. 7 illustrates locking member 56 positioned within opening 69 of wall 33 and constrained by resilient members 78. The resilient members allow the locking member to articulate between a locked and unlocked position and bias the locking member in an unlocked configuration. In one aspect, the resilient members are defined by a portion of wall 33. Alternatively, the resilient members are sheets of resilient material mated to the upper and lower surfaces of wall 33.

Figure 8:
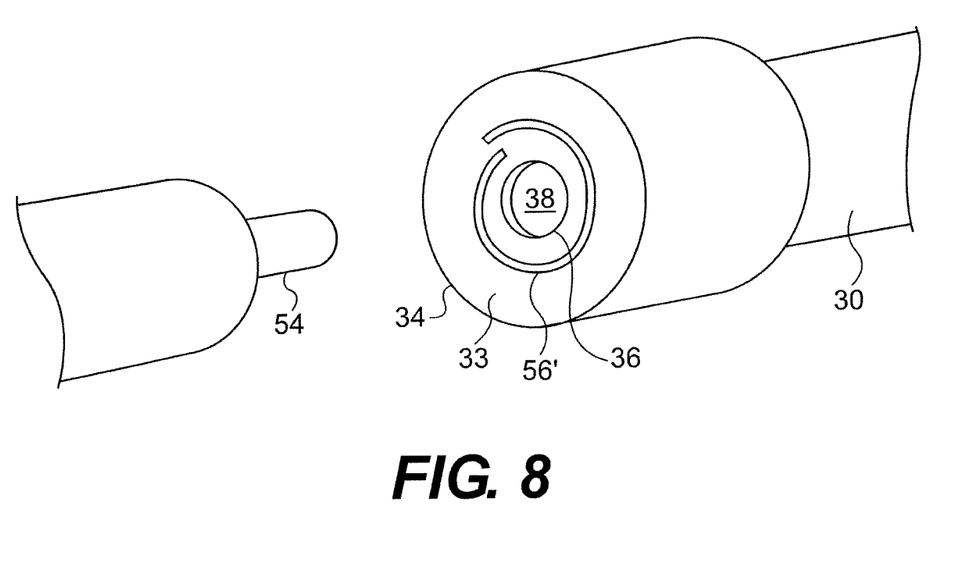
FIG. 8 illustrates a cross-sectional view of a spring locking member positioned within the wall of the first engaging member.

In yet another embodiment, the body of the locking member is defined by a spring. FIG. 8 illustrates a cross-sectional view of first engaging member 26 having a spring locking member 56' positioned within wall 33. Wall 33 can be formed of flexible and/or elastic type material such that as the spring is compressed/released the dimensions of the inner and outer surfaces 36, 34 of wall 33 contract/expand. In particular, spring locking member 56' can be chosen such that at least a portion of outer surface 34 is larger than the inner surface of catheter 30. When positioned within catheter 30, spring locking member 56' compresses, changing the dimensions of cavity 38 of the first engaging member. In particular, when the detachable link is positioned within catheter 30, at least a portion of inner surface 36 of cavity 38 can have a size and shape configured to mate with the outer surface of the second engaging member. In one aspect, spring locking member 56' is a leaf-type spring as illustrated in FIG. 8. Alternatively, the spring locking member can be defined by one or more coil-type springs positioned in wall 33.

While FIGS. 5A through 8 illustrate a single locking member, two or more than two locking members could be used with system 20. For example, multiple locking members could be located along the length and/or around the circumference of the first engaging member. In addition, multiple recesses 58 can be positioned on the second engaging member to receive the locking members. In one aspect, a single recess can extend around the circumference of the second engaging member and receive multiple locking members.

Figure 9A:
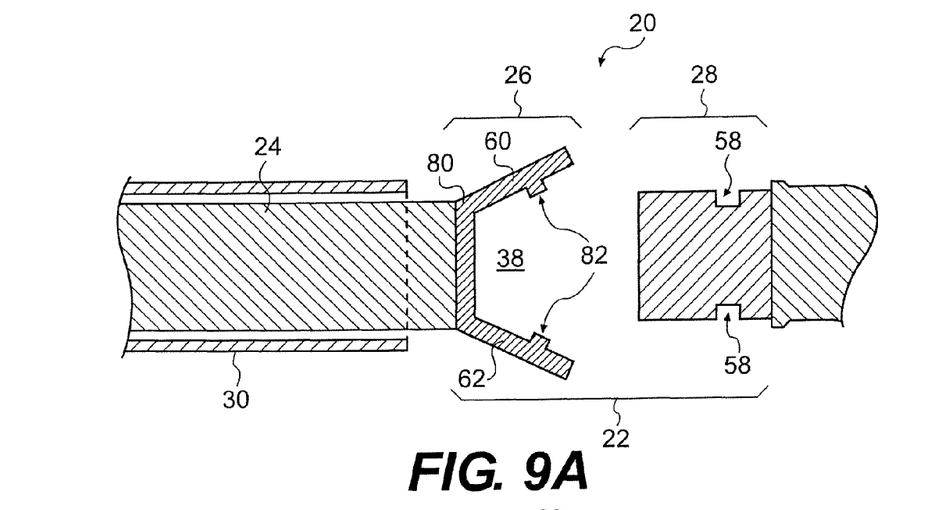
FIG. 9A illustrates a cross-sectional view of another embodiment of the implant delivery system in an unmated configuration.

In yet another embodiment of the detachable link described herein, the wall of the first engaging member can be defined at least in part by articulating arms. FIG. 9A illustrates first arm 60 and a second arm 62 extending around cavity 38. The arms can be defined by ridged or semi-ridged, elongate bodies extending distally from the body of the first engaging member. Between arms 60, 62 the first engaging member can have open sides. While the illustrated embodiment depicts two arms, three or more than three arms can be used with system 20.

Figure 9B:
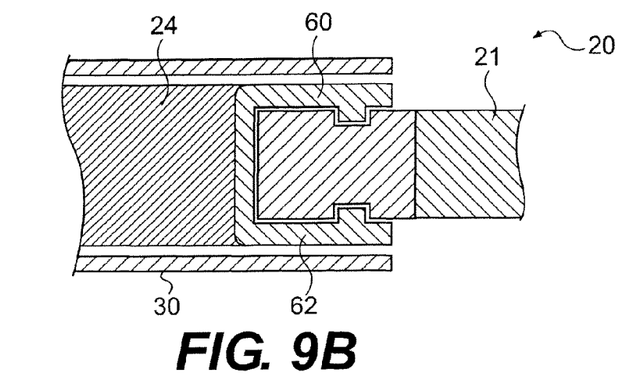
FIG. 9B illustrates a cross-sectional view of FIG. 9A in a mated configuration inside the catheter.

The first arm 60 and the second arm 62 can move between a first unlocked position (FIG. 9A) and a second locked position (FIG. 9B). In the unlocked position the arms are spaced sufficiently to allow the second engaging member to move between the first and second arms. When the detachable link in inserted into the catheter, the catheter walls can contact the first and second arms and move the arms toward one another. With the second engaging member positioned between the arms, the catheter 30 can cause the inner surfaces of the arms to contact the outer surface of the second engaging member and mate therewith.

The arms and second engaging member can mate via a mechanical and/or frictional connection. In one aspect, the arms include protrusions 82 which can mechanically mate with recesses 58 in the outer surface of the second engaging member.

In one aspect, arms 60, 62 are mated to the first engaging member body via a pivot point 80 that allows the arms to move between the locked and unlocked position. The pivot point can be a hinge, such as, for example, a living hinge. In one aspect, pivot point 80 is a living hinge which biases the arms in the unlocked position. Alternatively, arms 60, 62 can be biased in the unlocked position using a spring or resilient material.

A variation of the embodiment in FIGS. 9A and 9B can include a single articulating arm and an opposed fixed arm (not illustrated). When the second engaging member is positioned between the arms the articulating arm can move toward the fixed arm to detachably lock the first and second engaging members to one another.

Further described herein are methods for delivering and detaching an implantable device. In one embodiment, an implantable device and delivery wire are provided, where a detachable link mates the implantable device to the delivery wire. The detachable link can comprise first and second engaging members configured to "lock" to one another while positioned a delivery catheter and configured to self-detach (or "unlock") after exiting the delivery catheter.

As described above, the detachable link can include a first expandable member configured to move between a first and second position. When the detachable link is mated within a catheter, the first expandable member can be in a second position such that the expandable member locks the first and second engaging members. Moving the detachable link through a distal opening in the catheter moves the expandable member from the second position to the first position and allows the first and second engaging members to self-detach.

Prior to insertion of the detachable link into a catheter, the first and second engaging members can be mated by a surgeon. Alternatively, the first and second engaging members can be delivered to the end user in a locked configuration. For example, the detachable link can be provided in a separate housing (e.g., an inserter) and moved into the catheter for delivery to a target anatomic site.

Further described herein is a method of manufacture. The method can include providing an elongate body having a lumen, a first engaging member, and a second engaging member. The method further includes aligning the first and second engaging members. For example, where the first and second engaging members have a male/female configuration, the step of aligning can include placing a portion of the second engaging member within the first engaging member. When the first and second engaging members are aligned, the method can include the step of locking the first and second engaging members to one another by placing the first and second engaging members in the lumen of the elongate body.

As mentioned above, the first engaging member can include expandable member adapted to move between a first position and a second position. In one aspect, the step of locking can include moving the expandable member from a first position to a second position by placing the first and second engaging members in the lumen of the elongate body.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. An implant delivery system, comprising:
   an elongate device defining an axial lumen; and
   an implantable device mated to a delivery wire via a detachable link slidably disposed within the axial lumen of the elongate device, the detachable link comprising first and second engaging members,
   the first engaging member having an inner surface, an outer surface, and a wall therebetween, wherein a portion of the wall radially expands or contracts to move between a first and a second position, wherein in the first position the wall portion forms a protrusion on the outer surface of the first engaging member, and in the second position the wall portion forms a protrusion on the inner surface of the first engaging member; and
   the second engaging member having an outer surface shaped and sized for receipt within the inner surface of the first engaging member when the wall portion is in the first position and wherein the second engaging member is shaped and sized to inhibit movement out of the inner surface of the first engaging member when the wall portion is in the second position.

2. The system of claim 1, wherein the wall portion is biased in the first position.

3. The system of claim 1, the wall defining a cavity adapted to receive the second engaging member.

4. The system of claim 1, wherein the wall is formed from a flexible, elastic, and/or compressible material.

5. The system of claim 1, wherein the wall is deformable.

6. The system of claim 1, wherein the outer surface of the second engaging member includes a recess adapted to receive a portion of the first engaging member when the wall portion is in the second position.

7. The system of claim 1, wherein the second engaging member is formed of a resilient material.

8. The system of claim 1, wherein the wall portion includes an articulating locking member.

9. The system of claim 1, wherein the first engaging member is attached to the delivery wire and the second engaging member is attached to the implantable device.

* * * * *